United States Patent
Beckmann

(10) Patent No.: US 9,708,388 B2
(45) Date of Patent: Jul. 18, 2017

(54) ANTIBODY LIGHT CHAINS

(71) Applicant: DUTALYS GMBH, Vienna (AT)

(72) Inventor: Roland Beckmann, Vienna (AT)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/391,853

(22) PCT Filed: Apr. 11, 2013

(86) PCT No.: PCT/EP2013/001065
§ 371 (c)(1),
(2) Date: Oct. 10, 2014

(87) PCT Pub. No.: WO2013/152860
PCT Pub. Date: Oct. 17, 2013

(65) Prior Publication Data
US 2015/0086538 A1    Mar. 26, 2015

(30) Foreign Application Priority Data

Apr. 11, 2012 (EP) .................................. 12002561

(51) Int. Cl.
*C07K 16/00* (2006.01)
(52) U.S. Cl.
CPC ........ *C07K 16/00* (2013.01); *C07K 2317/515* (2013.01); *C07K 2317/52* (2013.01); *C07K 2317/55* (2013.01); *C07K 2317/94* (2013.01)
(58) Field of Classification Search
CPC .............. C07K 16/00; C07K 2317/515; C07K 2317/52; C07K 2317/55; C07K 2317/94
USPC ........ 424/133.1; 435/320.1, 69.5; 530/387.3; 536/25.53
See application file for complete search history.

(56) References Cited

U.S. PATENT DOCUMENTS

| | | | |
|---|---|---|---|
| 2010/0047171 A1* | 2/2010 | Beckmann ........... | C07K 16/244 424/9.1 |
| 2011/0044986 A1* | 2/2011 | Biere-Citron ......... | C07K 16/18 424/139.1 |
| 2011/0150888 A1* | 6/2011 | Foltz .................. | A61K 38/1816 424/139.1 |
| 2011/0274691 A1* | 11/2011 | Arvedson .............. | C07K 16/28 424/139.1 |
| 2013/0089554 A1* | 4/2013 | Blankenship ...... | C07K 16/2818 424/136.1 |
| 2013/0095097 A1* | 4/2013 | Blankenship ...... | C07K 16/2818 424/133.1 |
| 2013/0129723 A1* | 5/2013 | Blankenship .......... | C07K 16/44 424/134.1 |
| 2013/0209475 A1* | 8/2013 | Richards ................ | C07K 16/18 424/139.1 |
| 2014/0356357 A1* | 12/2014 | Ariaans ................ | C07K 16/241 424/133.1 |
| 2014/0359902 A1* | 12/2014 | Ariaans ................ | C07K 16/241 800/288 |
| 2014/0370020 A1* | 12/2014 | Kuramochi ........ | C07K 16/2866 424/136.1 |
| 2015/0166649 A1* | 6/2015 | Ariaans ................ | C07K 16/241 424/133.1 |
| 2015/0274844 A1* | 10/2015 | Blankenship ...... | C07K 16/2818 424/135.1 |
| 2016/0033511 A1* | 2/2016 | Pannell ............ | G01N 33/57438 514/266.4 |
| 2016/0083470 A1* | 3/2016 | Arvedson .............. | C07K 16/28 424/133.1 |

FOREIGN PATENT DOCUMENTS

| | | |
|---|---|---|
| WO | 2010062896 A1 | 6/2010 |
| WO | 2012016227 A2 | 2/2012 |

OTHER PUBLICATIONS

Infante et al. (JBC 254:9006-9016 (1979)).*
Dariavach et al. (PNAS 84(24):9074-9078 (1987)).*
The International Search Report and Written Opinion mailed Nov. 6, 2013 in PCT/EP2013/001065.
Liu et al., "Effect of the light chain C-terminal serine residue on disulfide bond susceptibility of human immunoglobulin G1•", Analytial Biochemistry, 2011, 408:277-283.
Shen et al., "Removal of a C-terminal serine residue proximal to the inter-chain disulfide bond of a human IgG1 lambda light chain mediates enhanced antibody stability and antibody dependent cell-mediated cytotoxicity", MABS, 2013, 5(3):418-431.
Communication pursuant to Article 94(3) EPC dated Feb. 9, 2016 issued in EP 13720231.3 (5 pages).

* cited by examiner

*Primary Examiner* — Lynn Bristol
(74) *Attorney, Agent, or Firm* — Prismatic Law Group, PLLC; Ronald Kamis

(57) ABSTRACT

The present invention relates to methods for improving biophysical properties, including the stability of antibody lambda light chains, to antibody lambda light chains with improved biophysical properties, including stability, nucleic acid and vectors encoding such antibody lambda light chains, and to uses of such antibody lambda light chains, nucleic acid and vectors.

15 Claims, 4 Drawing Sheets

Figure 1: SDS-PAGE
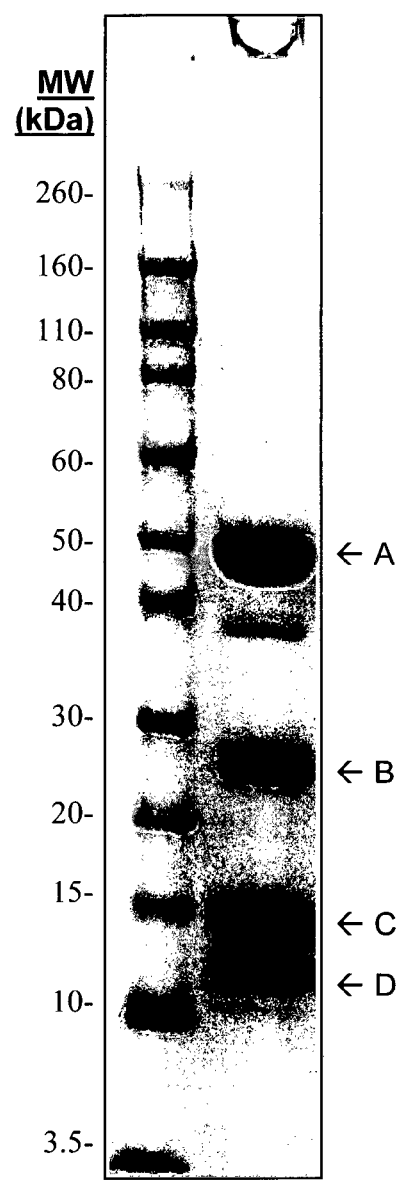

Figures 2A-2B: Example of differential scanning calorimetry data
Figure 2A: wild-type CL2
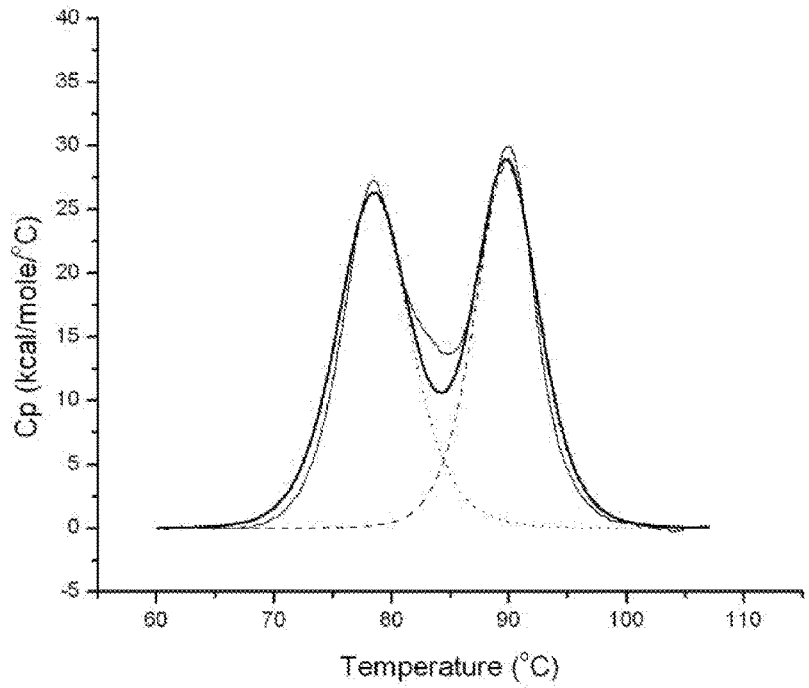
Figure 2B: wild-type CL7
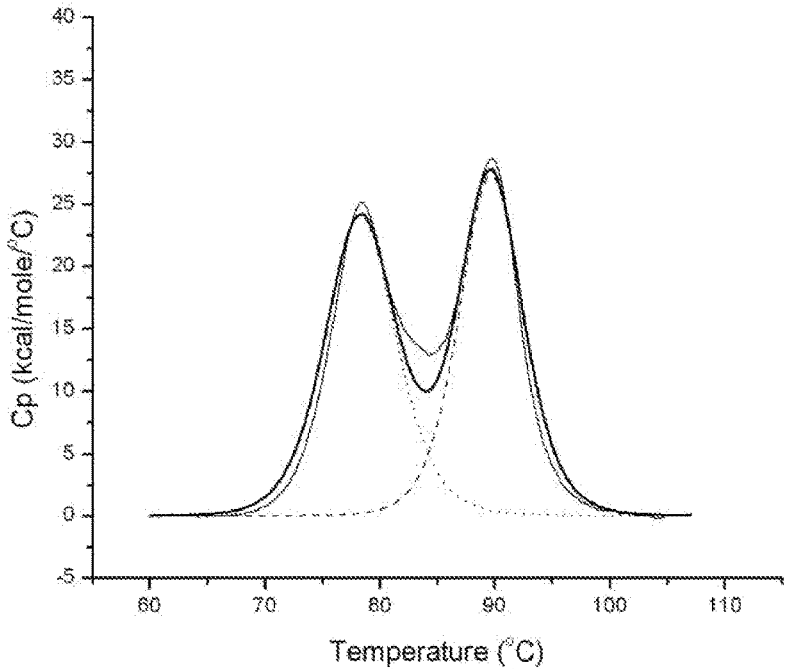

Figures 2C-2D: Example of differential scanning calorimetry data
Figure 2C: engineered CL27ΔS
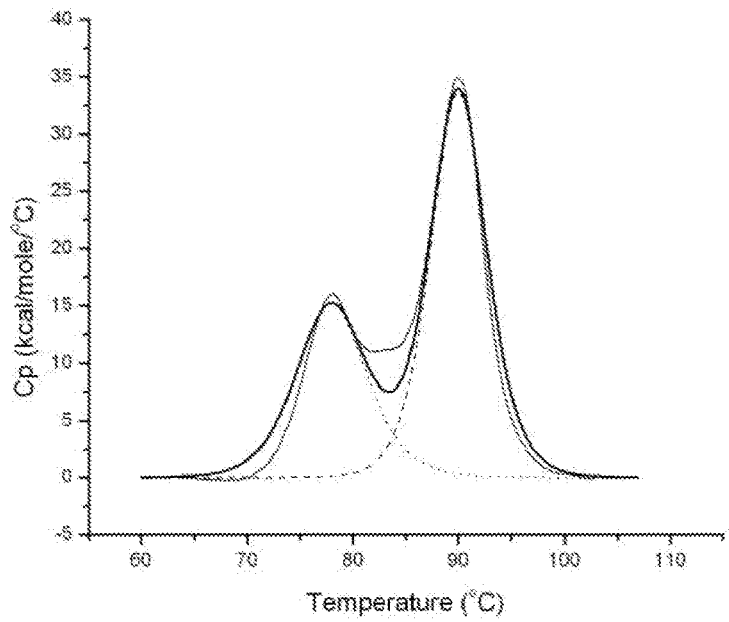
Figure 2D: engineered CL6ΔS
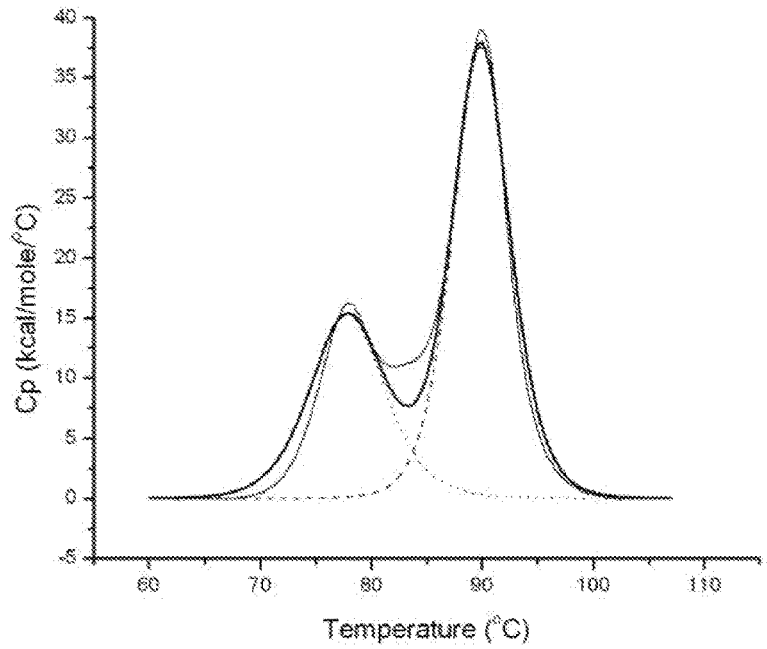

Figure 3: Sequence Overview

| Kabat | 110 | 120 | 130 | 140 | 150 | 160 |
|---|---|---|---|---|---|---|
| CL2 | GQPK | AAPSVTLFPP | SSEELQANKA | TLVCLISDFY | PGAVTVAWKA | DSSPVKAGVE |
| CL6 | GQPK | AAPSVTLFPP | SSEELQANKA | TLVCLISDFY | PGAVKVAWKA | DGSPVNTGVE |
| CL7 | GQPK | AAPSVTLFPP | SSEELQANKA | TLVCLVSDFY | PGAVTVAWKA | DGSPVKVGVE |
| CL27 | GQPK | AAPSVTLFPP | SSEELQANKA | TLVCLISDFY | PGAVTVAWKA | DGSPVKVGVE |
| CL67 | GQPK | AAPSVTLFPP | SSEELQANKA | TLVCLISDFY | PGAVKVAWKA | DGSPVNTGVE |
| CL6ΔS | GQPK | AAPSVTLFPP | SSEELQANKA | TLVCLISDFY | PGAVKVAWKA | DGSPVNTGVE |
| CL7ΔS | GQPK | AAPSVTLFPP | SSEELQANKA | TLVCLISDFY | PGAVTVAWKA | DGSPVKVGVE |
| CL27ΔS | GQPK | AAPSVTLFPP | SSEELQANKA | TLVCLISDFY | PGAVTVAWKA | DGSPVKVGVE |
| CL67ΔS | GQPK | AAPSVTLFPP | SSEELQANKA | TLVCLISDFY | PGAVKVAWKA | DGSPVNTGVE |

| Kabat | 170 | 180 | 190 | 200 | 210 | 215 |
|---|---|---|---|---|---|---|
| CL2 | TTTPSKQS N | NKYAASSYLS | LTPEQWKSHR | SYSCQVTHEG | STVEKTVA | PTECS |
| CL6 | TTTPSKQS N | NKYAASSYLS | LTPEQWKSHR | SYSCQVTHEG | STVEKTVA | PAECS |
| CL7 | TTKPSKQS N | NKYAASSYLS | LTPEQWKSHR | SYSCRVTHEG | STVEKTVA | PAECS |
| CL27 | TTKPSKQS N | NKYAASSYLS | LTPEQWKSHR | SYSCRVTHEG | STVEKTVA | PAECS |
| CL67 | TTTPSKQS N | NKYAASSYLS | LTPEQWKSHR | SYSCRVTHEG | STVEKTVA | PAECS |
| CL6ΔS | TTTPSKQS N | NKYAASSYLS | LTPEQWKSHR | SYSCQVTHEG | STVEKTVA | PAEC |
| CL7ΔS | TTKPSKQS N | NKYAASSYLS | LTPEQWKSHR | SYSCRVTHEG | STVEKTVA | PAEC |
| CL27ΔS | TTKPSKQS N | NKYAASSYLS | LTPEQWKSHR | SYSCRVTHEG | STVEKTVA | PAEC |
| CL67ΔS | TTTPSKQS N | NKYAASSYLS | LTPEQWKSHR | SYSCRVTHEG | STVEKTVA | PAEC |

SEQUENCE LISTING

```
<160> NUMBER OF SEQ ID NOS: 9

<210> SEQ ID NO 1
<211> LENGTH: 106
<212> TYPE: PRT
<213> ORGANISM: Homo sapiens

<400> SEQUENCE: 1

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 2
```

<211> LENGTH: 106
<212> TYPE: PRT
<213> ORGANISM: Homo sapiens

<400> SEQUENCE: 2

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105

<210> SEQ ID NO 3
<211> LENGTH: 106
<212> TYPE: PRT
<213> ORGANISM: Homo sapiens

<400> SEQUENCE: 3

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 4
<211> LENGTH: 106
<212> TYPE: PRT
<213> ORGANISM: Homo sapiens

<400> SEQUENCE: 4

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

```
Ser His Arg Ser Tyr Ser Cys Arg Val Thr His Glu Gly Ser Thr Val
            85                  90                  95

Glu Lys Thr Val Ala Pro Ala Glu Cys Ser
            100                 105

<210> SEQ ID NO 5
<211> LENGTH: 106
<212> TYPE: PRT
<213> ORGANISM: Homo sapiens

<400> SEQUENCE: 5

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
            85                  90                  95

Glu Lys Thr Val Ala Pro Ala Glu Cys Ser
            100                 105

<210> SEQ ID NO 6
<211> LENGTH: 105
<212> TYPE: PRT
<213> ORGANISM: Homo sapiens

<400> SEQUENCE: 6

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
            85                  90                  95

Glu Lys Thr Val Ala Pro Ala Glu Cys
            100                 105

<210> SEQ ID NO 7
<211> LENGTH: 105
<212> TYPE: PRT
<213> ORGANISM: Homo sapiens

<400> SEQUENCE: 7

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
```

```
                    35                  40                  45
Val Lys Val Gly Val Glu Thr Thr Lys Pro Ser Lys Gln Ser Asn Asn
     50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Arg Val Thr His Glu Gly Ser Thr Val
                     85                  90                  95

Glu Lys Thr Val Ala Pro Ala Glu Cys
                100                 105

<210> SEQ ID NO 8
<211> LENGTH: 105
<212> TYPE: PRT
<213> ORGANISM: Homo sapiens

<400> SEQUENCE: 8

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Gly Ser Pro
            35                  40                  45

Val Lys Val Gly Val Glu Thr Thr Lys Pro Ser Lys Gln Ser Asn Asn
     50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Arg Val Thr His Glu Gly Ser Thr Val
                     85                  90                  95

Glu Lys Thr Val Ala Pro Ala Glu Cys
                100                 105

<210> SEQ ID NO 9
<211> LENGTH: 105
<212> TYPE: PRT
<213> ORGANISM: Homo sapiens

<400> SEQUENCE: 9

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Lys Val Ala Trp Lys Ala Asp Gly Ser Pro
            35                  40                  45

Val Asn Thr Gly Val Glu Thr Thr Thr Pro Ser Lys Gln Ser Asn Asn
     50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Arg Val Thr His Glu Gly Ser Thr Val
                     85                  90                  95

Glu Lys Thr Val Ala Pro Ala Glu Cys
                100                 105
```

ANTIBODY LIGHT CHAINS

CROSS REFERENCE TO RELATED APPLICATIONS

The present invention is filed under 35 U.S.C. §371 as the U.S. national phase of International Application No. PCT/EP2013/001065, filed Apr. 11, 2013, which designated the U.S. and claims the benefit of priority to European Patent Application No. 12002561.4, filed Apr. 11, 2012, each of which is hereby incorporated in its entirety including all tables, figures and claims.

FIELD OF THE INVENTION

The present invention relates to methods for improving biophysical properties, including the stability of antibody lambda light chains, to antibody lambda light chains with improved biophysical properties, including stability, nucleic acid and vectors encoding such antibody lambda light chains, and to uses of such antibody lambda light chains, nucleic acid and vectors.

SEQUENCE LISTING

The instant application contains a Sequence Listing which has been submitted in ASCII format via EFS-Web and is hereby incorporated by reference in its entirety. Said ASCII copy, created on Jul. 28, 2016, is named WRPATDUT4_SeqListing.txt and is 9 kilobytes in size.

BACKGROUND OF THE INVENTION

This invention relates to a novel approach for improving biophysical properties of antibodies, including a method for the stabilization of antibodies.

The biophysical stability of monoclonal antibodies is an important determinant of their usefulness and commercial value for several reasons (reviewed, among others, by Garber and Demarest, 2007, and by Honegger, 2008). First, high biophysical stability can result in high antibody expression yield in recombinant systems. High expression yield can facilitate antibody selection and screening, for example by enhancing the display level of antibodies on bacteriophages and by enhancing the soluble yield of antibodies in small-scale E. coli cultures, and therefore lead to the discovery of better antibody molecules. High expression yield can also be important in making the manufacturing of commercially available monoclonal antibodies economically viable by allowing a sufficiently small production scale suitable for the application. In monoclonal antibodies intended for therapeutic applications, high biophysical stability can be important as it can be associated with high solubility, therefore enabling antibodies to be efficiently formulated at high concentrations into drugs. Also in therapeutic monoclonal antibodies, high biophysical stability can be important for avoiding antibody aggregation during various manufacturing steps (including expression, purification, acid-mediated virus-deactivation and formulation) and during storage. The avoidance of aggregation is not only important to maximizing the economic viability of an antibody drug production process but is also thought to play an important role in minimizing the potential immunogenicity of antibody drugs in patients. Finally, also in therapeutic monoclonal antibodies, high biophysical stability is important in achieving a long antibody half-life both in patients and in disease models.

In recognition of the importance of high biophysical stability of monoclonal antibodies, researchers have aimed to improve the biophysical stability of monoclonal antibodies for the past several years. Research efforts have aimed to stabilize antibody constant domains, isolated antibody variable domains (especially autonomous VH domains known as VHH domains, VH domain antibodies, nanobodies or monobodies; but also autonomous VL domains), as well as heterodimeric antibodies comprising one VH and one VL domain. The read-out employed in such stabilization work has included increased expression yield, increased solubility of the expressed antibodies, increased levels of display in phage display libraries, increased resistance to denaturant-induced unfolding and increased resistance to heat-induced unfolding (known as thermal stability). In order to obtain antibody variable regions with improved biophysical stability, a variety of approaches has been taken that can be categorized as follows.

Researchers have employed specific antibody selection conditions, such as phage display with heat- or denaturant-induced stress during panning, to select antibody clones with superior biophysical properties, including reduced aggregation (Jung et al., 1999; Jespers et al., 2004(A); Dudgeon et al., 2008).

Researchers have employed specific antibody screening conditions, such as E. coli expression in the presence of reducing agents or fluorescent antigens able to permeate into the periplasm, or heating of secreted antibody clones in microtiter plates during antigen-specific ELISA screening, to select antibody clones with superior biophysical properties, including faster folding and greater thermal stability (Ribnicky et al., 2007; Martineau and Betton, 1999; Demarest et al., 2006).

Heterodimeric VH-VL antibody fragments have been stabilized by the addition of various entities such as chemical cross-linkers, peptide linkers to create single-chain Fv and single-chain Fab fragments, interchain disulphide bonds to create disulphide-stabilized Fv fragments, and heterodimeric coiled coils to create helix-stabilized Fv fragments (reviewed by Arndt et al., 2001).

Researchers have mutated framework residues at the VH-VL interface of heterodimeric VH-VL antibody fragments to obtain antibodies with greater resistance to denaturant-induced unfolding (Tan et al., 1998).

Heterodimeric VH-VL antibody fragments have been stabilized by increasing the hydrophilicity of solvent-exposed framework region residues. In some cases this has been done by disrupting hydrophobic patches at the antibody variable/constant domain interface (Nieba et al., 1997).

Autonomous VH domains have been stabilized by mutating positions otherwise contributing to the light chain interface, thereby improving solubility of this region that is buried in heterodimeric VH-VL antibodies (Davies and Riechmann, 1994; Riechmann, 1996; Bathelemy et al., 2007).

Autonomous VH domains have been stabilized by engineering additional intradomain disulphide bonds within the framework region (Davies and Riechmann, 1996) or between CDRs (Tanha et al., 2001).

In autonomous human and camelid VH domains, the CDR3 has been engineered to compensate for the hydrophobicity of the former light chain interface and to obtain better solubility of these domains (Tanha et al., 2001; Jespers et al., 2004(B); Dottorini et al., 2004).

In autonomous VL domains, a position in CDR1 (residue 32) and two positions in CDR2 (residues 50 and 56) have been engineered to increase the stability of the isolated VL domains towards denaturant-induced unfolding and to improve the feasibility of their potential use as disulphide-free intrabodies (Steipe, 1994; Ohage et al., 1997; Proba et al., 1998; Ohage and Steipe, 1999); all numbering according to Kabat (Kabat and Wu, 1991; Kabat et al., 1991).

Germline genes from which VH or VL antibody domains are derived have been identified and analysed, and their sequences compiled into databases (Lefranc et al., 1999; Retter et al., 2005), and family-specific key residues have been identified that are critical for the family-specific folding and side-chain-packing within the VH or within the VL domain (Ewert et al., 2003(A)). Then, by aligning germline genes, protein consensus sequences have been generated for variable domains that contain more of the family-specific key residues than variable domains derived from individual germline genes and as a result have potentially improved biophysical properties over variable domains derived from individual germline genes (Steipe et al., 1994; reviewed by Wörn and Plückthun, 2001). Resulting human variable domain consensus sequences have been used in the humanization of animal-derived monoclonal antibodies (for example, Carter et al., 1992) and in the construction of synthetic human antibody libraries (for example, Knappik et al., 2000).

11) Based on consensus sequences, human VH and VL germline families have been characterized, families with inferior or superior biophysical properties have been identified, and individual framework region residues responsible for the inferior or superior properties have been pin-pointed (for example, Ewert et al., 2003(A)). This has allowed researchers to generate antibodies with improved biophysical properties in several ways:

Human antibody clones of known specificity have been stabilized by human-to-human CDR grafting: Antigen-specific CDR loops and selected putative specificity-enhancing framework region residues from a donor clone derived from a human germline gene associated with inferior biophysical properties were transplanted onto a human acceptor framework associated with superior biophysical properties (Jung and Plückthun, 1997).

Human antibody clones of known specificity have been stabilized by framework-engineering: A set of framework region residues thought to be responsible for inferior properties of one germline family has been exchanged for a set of different framework region residues found in a germline family associated with superior properties, thereby improving the biophysical properties of the antibody clone while retaining most of the original framework region sequences and while retaining the specificity (Ewert et al., 2003(B)).

Based on the ranking of the biophysical properties of human germline family consensus genes in the context of VH-VL pairings, researchers have suggested that synthetic antibody libraries should be prepared in which only those germline families with a consensus that had shown superior biophysical properties in the VH-VL pairings (VH1, VH3 and VH5 as well as Vkappa1, Vkappa3 and Vlambda) should be represented (Ewert et al., 2003(A)).

Researchers have generated synthetic antibody libraries in which all germline families were represented, but all clones derived from a VH germline family associated with inferior biophysical properties (VH4) contained a point-mutation in the framework region designed to improve the biophysical properties of these clones (Rothe et al., 2008).

Researchers have generated synthetic libraries of VH-VL heterodimeric antibodies based on a single synthetic VH framework and a single synthetic VL framework (for example, Lee et al., 2004; Fellouse et al., 2007) or on a single synthetic VH framework and multiple synthetic VL frameworks (for example, Silacci et al., 2005) known for their favourable biophysical framework properties.

Efforts have been made to obtain naturally occurring and therefore potentially stable CDR conformations in synthetic libraries of single domain antibodies and VH-VL heterodimeric antibodies, in order to give the antibodies nature-like and good, albeit not especially improved, biophysical properties. To this end, some CDR positions that are known to be determinants of specific canonical CDR structures (Chothia et al., 1992; Tomlinson et al., 1995; Al-Lazikani et al., 1997) have been left undiversified or subjected to restricted diversification in many published synthetic antibody libraries, maintaining them as the dominant residue or residues most frequently found in the germline family context of the particular VH or VL domain on which the library is based. Among such positions that bear canonical-structure-determining CDR residues and that have been left undiversified or subjected to restricted diversification in published antibody libraries are positions 27, 29 and 34 in HCDR1, positions 52a, 54 and 55 in HCDR2, and positions 94 and 101 in HCDR3, as well as positions 90 and 95 in the LCDR3 of Vkappa domains (all numbering according to Kabat (Kabat and Wu, 1991)).

Also in efforts to obtain natural and potentially stable CDR conformations in synthetic libraries of single domain antibodies and VH-VL heterodimeric antibodies, other CDR residues buried within the VH domain or within the VL domain, which are naturally conserved independently of different specific canonical CDR structures, have been left undiversified or subjected to restricted diversification in some synthetic antibody libraries, maintaining them as the dominant amino acid most frequently found in nature (for example, VH position 51 in HCDR2 has been kept undiversified in several published synthetic human antibody libraries, bearing an invariant Ile).

However, despite that fact that many attempts have been made to provide stable antibodies and/or to stabilize existing antibodies, so far these attempts have had limited success.

Thus, there was still a large unmet need to provide novel methods for the stabilization of antibodies, including for the generation of antibody libraries. One important unmet need was that of stable human lambda antibodies exhibiting high thermal stability of the variable region but at the same time low levels of Fab constant region degradation during phage library production and during E. coli expression.

One application where Fab constant region degradation in human lambda antibodies has been particularly problematic is that of phage library production. Some ways of isolating antibody drug candidate molecules involve the generation of phage libraries that display antibody fragments, particularly Fab fragments on the surface of phage particles produced in E. coli, where the Fab fragment is expressed and incorporated or attached to the phage particle during phage assembly. This process requires that Fab fragments are displayed efficiently on the surface of the phage particle. The efficiency of display is usually dependent on intact Fab constant domains following expression in E. coli, because attachment to the phage particle is either mediated by a protein linker that forms an extension of one of the constant domains and is directly fused to a phage coat protein, or by a disulphide bond that is formed between a cysteine residue in the C-terminal region of one of the constant domains and a free cysteine residue engineered into one of the phage coat proteins. Incomplete expression, truncation or degradation (hereinafter simply referred to as degradation) of Fab constant regions during expression in E. coli would therefore result in inefficient display: In antibody clones where in the majority of molecules the constant regions are degraded during *E. coli* expression, only the minority can be displayed as intact Fab fragments, leading to inefficient phage library production. Importantly, if constant region degradation varies between library members, this leads to an under-representation of clones with more degraded constant regions in the displayed repertoire and therefore a lesser chance of isolating such clones as drug candidates.

Another application where Fab constant region degradation in human lambda antibodies has been particularly problematic is that of recombinant *E. coli* expression for antibody screening purposes. Some ways of isolating antibody drug candidates involve the screening of antibody clones as Fab fragments expressed in *E. coli*. In such screening campaigns, usually hundreds or thousands of antibody clones are expressed in individual wells of microtiter plates, and subjected to various analyses such as ELISA, SPR or biological assays. The read-out of these analyses is typically a signal that is correlated to the usefulness of the antibody clone, such as specificity or affinity. The intensity of the signal obtained in these analyses typically depends on antibody affinity and on the apparent concentration in which an antibody clone is present in the well of the microtiter plate. This concentration is commonly detected through secondary antibodies that bind to epitopes in the primary antibody's constant regions or to epitope tags fused to the primary antibody's constant regions. In both cases, detection depends on the presence and usually intact nature of the primary antibody's constant regions. If the constant regions are degraded during expression in *E. coli*, the concentration of the detected epitopes does not reflect the concentration at which the antibody was expressed and may not reflect the concentration of binding sites, formed by the variable regions that are present in the well of the microtiter plate. Again it is important to note that if constant region degradation varies between library members, this leads to a lower apparent concentration of clones with more degraded constant regions in the microtiter plate and therefore a lesser chance of isolating such clones as drug candidates.

The solution for this problem that has been provided by the present invention, i.e. the modification of particular residues in the constant region of lambda light chains, has so far not been achieved or suggested by the prior art.

SUMMARY OF THE INVENTION

The present invention relates to a method for improving biophysical properties, including the stability of antibody lambda light chains and to antibody lambda light chains with improved biophysical properties, such as stability.

In a first aspect, the present invention relates to a method for modifying the constant region of a parental antibody lambda light chain, comprising at least one of the following steps:
 (a) deleting the C-terminal amino acid residue Serine;
 (b) in the case of a lambda light chain with a constant domain Clambda2, making the following amino acid residue exchange: S152G, and optionally one or more of the following amino acid residue exchanges: A157V, T163K, Q195R, and T212A;
 (c) in the case of a lambda light chain with a constant domain Clambda7, making the following amino acid residue exchange: V136I, and optionally one or more of the following amino acid residue exchanges: T145K, K156N, V157T, and K163T.

In a second aspect, the present invention relates to a constant region of an antibody lambda light chain, wherein said constant region is selected from the group of:
 (i) a constant region of an antibody lambda light chain, wherein the C-terminus is amino acid residue 214;
 (ii) a constant region of an antibody lambda light chain of the type Clambda2, wherein said constant region has a glycine residue at position 152 and at least one of the following amino acid residues: 157V, 163K, 195R, and 212A;
 (iii) a constant region of an antibody lambda light chain of the type Clambda7, wherein said constant region has an isoleucine residue at position 136 and optionally one or more of the following amino acid residues: 145K, 156N, 157T, and 163T;
 (iv) a constant region exhibiting the features of both (i) and (ii); and
 (v) a constant region exhibiting the features of both (i) and (iii).

In a third aspect, the invention relates to an antibody or antibody fragment comprising at least the constant region of the present invention.

In a fourth aspect, the present invention relates to the use of a constant region of an antibody lambda light chain according to the present invention in the construction of an antibody or antibody fragment, comprising the step of attaching said constant region to an antibody variable domain.

In a fifth aspect, the present invention relates to nucleic acid sequence encoding the constant region of an antibody lambda light chain according to the present invention, or the antibody or antibody fragment of the present invention.

In a sixth aspect, the present invention relates to a vector comprising the nucleic acid sequence according to the present invention.

In a seventh aspect, the present invention relates to a host cell comprising the nucleic acid sequence according to the present invention, or the vector according to the present invention.

In an eight aspect, the present invention relates to a method for generating the constant region of the present invention, or the antibody or functional fragment thereof of to the present invention, comprising the step of expressing the nucleic acid sequence according to the present invention, or the vector according to the present invention, either in vitro of from an appropriate host cell, including the host cell according to the present invention.

In a ninth aspect, the present invention relates to pharmaceutical compositions comprising an antibody molecule or functional fragment thereof comprising the constant region of an antibody lambda light chain according to the present invention, and optionally a pharmaceutically acceptable carrier and/or excipient.

BRIEF DESCRIPTION OF THE DRAWINGS

FIG. 1 shows an SDS-PAGE gel showing the chromatographic separation of a mixture of full-length and degraded Fab fragments and/or VH-CH1 and VL-CL1 chains. A: full Fab; B: full HC (top) and full LC (bottom); C: degradation product comprising VH; D: degradation product comprising VL FIG. 2 shows the results of differential scanning calorimetry experiments: (A) A: wild-type CL2; (B): wild-type CL7; (C): engineered CL27ΔS; (D): engineered CL6ΔS.

FIG. 3 contains sequence information for the parental constant domains CL2 (SEQ ID NO:1), CL6 (SEQ ID NO:2), and CL7 (SEQ ID NO:3), and for mutant constant domains CL27 (SEQ ID NO:4), CL67 (SEQ ID NO:5), CL6ΔS (SEQ ID NO:6), CL7ΔS (SEQ ID NO:7), CL27ΔS (SEQ ID NO:8), and CL67ΔS (SEQ ID NO:9). Numbering is according to Kabat, provided that in case of an inconsistency between the numbers used herein and Kabat the numbering shown in FIG. 3 shall be used. Positions to be exchanged/deleted are indicated by bold letters.

DETAILED DESCRIPTION OF THE INVENTION

The peculiarity of this invention compared to former approaches for stabilizing antibodies is the so far unknown effect of minor modifications to Clambda constant domain residues, including highly conserved residues, which results in antibodies with improved properties.

In a first aspect, the present invention relates to a method for modifying the constant region of a parental antibody lambda light chain, comprising at least one of the following steps:
  (a) deleting the C-terminal amino acid residue serine;
  (b) in the case of a lambda light chain with a constant domain Clambda2, making the following amino acid residue exchange: S152G, and optionally one or more of the following amino acid residue exchanges: A157V, T163K, Q195R, and T212A;
  (c) in the case of a lambda light chain with a constant domain Clambda7, making the following amino acid residue exchange: V136I, and optionally one or more of the following amino acid residue exchanges: T145K, K156N, V157T, and K163T.

As used herein, the term "antibody" refers to an immunoglobulin (Ig) molecule that is defined as a protein belonging to the class IgG, IgM, IgE, IgA, or IgD (or any subclass thereof), which includes all conventionally known antibodies and functional fragments thereof. A "functional fragment" of an antibody/immunoglobulin molecule hereby is defined as a fragment of an antibody/immunoglobulin molecule (e.g., a variable region of an IgG) that retains the antigen-binding region. An "antigen-binding region" of an antibody typically is found in one or more hypervariable region(s) (or complementarity-determining region, "CDR") of an antibody molecule, i.e. the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320). A preferred class of antibody molecules for use in the present invention is IgG.

"Functional fragments" of the invention include the domain of a F(ab')2 fragment, a Fab fragment, scFv or constructs comprising single immunoglobulin variable domains or single domain antibody polypeptides, e.g. single heavy chain variable domains or single light chain variable domains. The F(ab')2 or Fab may be engineered to minimize or completely remove the intermolecular disulphide interactions that occur between the CH1 and CL domains.

An antibody may be derived from immunizing an animal, or from a recombinant antibody library, including an antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254:67; and U.S. Pat. No. 6,300,064 issued to Knappik et al.

As used herein, a binding molecule is "specific to/for", "specifically recognizes", or "specifically binds to" a target, such as a target biomolecule (or an epitope of such biomolecule), when such binding molecule is able to discriminate between such target biomolecule and one or more reference molecule(s), since binding specificity is not an absolute, but a relative property. In its most general form (and when no defined reference is mentioned), "specific binding" is referring to the ability of the binding molecule to discriminate between the target biomolecule of interest and an unrelated biomolecule, as determined, for example, in accordance with a specificity assay methods known in the art. Such methods comprise, but are not limited to Western blots, ELISA, RIA, ECL, IRMA tests and peptide scans. For example, a standard ELISA assay can be carried out. The scoring may be carried out by standard colour development (e.g. secondary antibody with horseradish peroxide and tetramethyl benzidine with hydrogen peroxide). The reaction in certain wells is scored by the optical density, for example, at 450 nm. Typical background (=negative reaction) may be about 0.1 OD; typical positive reaction may be about 1 OD. This means the ratio between a positive and a negative score can be 10-fold or higher. Typically, determination of binding specificity is performed by using not a single reference biomolecule, but a set of about three to five unrelated biomolecules, such as milk powder, BSA, transferrin or the like.

In the context of the present invention, the term "about" or "approximately" means between 90% and 110% of a given value or range.

However, "specific binding" also may refer to the ability of a binding molecule to discriminate between the target biomolecule and one or more closely related biomolecule(s), which are used as reference points. Additionally, "specific binding" may relate to the ability of a binding molecule to discriminate between different parts of its target antigen, e.g. different domains, regions or epitopes of the target biomolecule, or between one or more key amino acid residues or stretches of amino acid residues of the target biomolecule.

In certain embodiments, the antibody or functional fragment of the present invention is selected from a single chain Fv fragment, a Fab fragment and an IgG.

Functional fragments according to the present invention may be Fv (Skerra, A. & Plückthun (1988). Assembly of a functional immunoglobulin Fv fragment in *Escherichia coli*. Science 240, 1038-1041), scFv (Bird, R. E., Hardman, K. D., Jacobson, J. W., Johnson, S., Kaufman, B. M., Lee, S. M., Lee, T., Pope, S. H., Riordan, G. S. & Whitlow, M. (1988). Single-chain antigen-binding proteins. Science 242, 423-426; Huston, J. S., Levinson, D., Mudgett-Hunter, M., Tai, M. S., Novotny, J., Margolies, M. N., Ridge, R. J., Bruccoleri, R. E., Haber, E., Crea, R. & Oppermann, H. (1988). Protein engineering of antibody binding sites: recovery of specific activity in an anti-digoxin single-chain Fv analogue produced in *Escherichia coli*. Proc. Natl. Acad. Sci. USA 85, 5879-5883), disulfide-linked Fv (Glockshuber, R., Malia, M., Pfitzinger, I. & Plückthun, A. (1992). A comparison of strategies to stabilize immunoglobulin Fv-fragments. Biochemistry 29, 1362-1367; Brinkmann, U., Reiter, Y., Jung, S., Lee, B. & Pastan, I. (1993). A recombinant immunotoxin containing a disulfide-stabilized Fv fragment. Proc. Natl. Acad. Sci. U.S.A. 90, 7538-7542), Fab, (Fab')2 fragments, single VH domains or other fragments well-known to the practitioner skilled in the art, which comprise at least one variable domain of an immunoglobulin or immunoglobulin fragment and have the ability to bind to a target.

In the context of the present invention, the terms "Clambda2", "Clambda6" and "Clambda7" and so on (or, alternatively, CL2, CL6, CL7) refer to the subclasses of human antibody constant domains as defined in Kabat (loc. cit.). In this context, the term "subclass" refers to a group of constant domains sharing a high degree of identity and similarity, which can be represented by a consensus sequence for a given subclass. The determination whether a given CL domain is belonging to a given Clambda subclass is made by alignment of the respective constant domain with all known human isotype sequences and determination of the highest degree of homology using a homology search matrix such as BLOSUM (Henikoff, S. & Henikoff, J. G. (1992). Amino acid substitution matrices from protein blocks. Proc. Natl. Acad. Sci. USA 89, 10915-10919). Methods for determining homologies and grouping of sequences according to homologies are well known to one of ordinary skill in the art.

The numbering system used for the constant domains according to the present invention is based on Kabat (loc. cit.), provided that in case of an inconsistency between the numbers used herein and Kabat the numbering shown in FIG. 3 shall be used.

In the context of the present invention, the phrase "deleting the C-terminal amino acid residue serine" refers to amino acid residue 215 (see FIG. 3), which is a conserved serine in human Clambda isotypes, which is deleted according to the present invention, so that the C-terminus of the Clambda protein ends with the amino acid residue found in position 214.

In certain embodiments, the constant region of a parental antibody lambda light chain is selected from the following subclasses: Clambda1, Clambda2, Clambda3, Clambda4, Clambda5, Clambda6, and Clambda7. In particular embodiments, the constant region of a parental antibody lambda light chain is selected from the following subclasses: Clambda1, Clambda2, Clambda3, and Clambda7. In particular embodiments, the constant region of a parental antibody lambda light chain is Clambda2. The sequences of Clambda2, Clambda6, and Clambda7 are shown in FIG. 3.

In a particular embodiment, the method comprises both steps (a) and (b).

In another particular embodiment, the method comprises both steps (a) and (c).

In a particular embodiment, in steps (b) all of the optional amino acid exchanges A157V, T163K, Q195R, and T212A are made:

In a particular embodiment, in steps (c) none of the optional amino acid exchanges is made.

In a particular embodiment, in steps (c) all of the optional amino acid exchanges T145K, K156N, V157T, and K163T are made.

In particular embodiments, the method of the present invention comprises the additional step of:
(d) expressing a nucleic acid sequence encoding an antibody or antibody fragment comprising a constant domain modified according to one or more of steps (a) to (c).

In a second aspect, the present invention relates to a constant region of an antibody lambda light chain, wherein said constant region is selected from the group of:
(i) a constant region of an antibody lambda light chain, wherein the C-terminus is amino acid residue 214;
(ii) a constant region of an antibody lambda light chain of the type Clambda2, wherein said constant region has a glycine residue at position 152 and at least one of the following amino acid residues: 157V, 163K, 195R, and 212A;
(iii) a constant region of an antibody lambda light chain of the type Clambda7, wherein said constant region has an isoleucine residue at position 136 and optionally one or more of the following amino acid residues: 145K, 156N, 157T, and 163T;
(iv) a constant region exhibiting the features of both (i) and (ii); and
(v) a constant region exhibiting the features of both (i) and (iii).

In certain embodiments, the C-terminus of a constant region of the present invention may be extended by additional non-immunoglobulin peptide or protein sequences, such as a peptide tag. In the context of the present invention, such constant regions are still regarded as a constant region, wherein the C-terminus is amino acid residue 214, as long as the amino acid residue immediately following in C-terminal direction is different from an amino acid residue found at amino acid residue 215 in a constant region of an antibody lambda light chain. In particular such embodiments, the amino acid residue immediately following in C-terminal direction is different from Serine.

In a particular embodiment, the constant region is an antibody lambda light chain domain of the type Clambda2, wherein the C-terminus of the constant region is amino acid residue 214, and wherein the constant region has an isoleucine residue at position 136 and optionally one or more of the following amino acid residues: 145K, 156N, 157T, and 163T.

In a particular embodiment, the constant region is an antibody lambda light chain domain of the type Clambda7, wherein the C-terminus of the constant region is amino acid residue 214, and wherein the constant region has a glycine residue at position 152 and optionally one or more of the following amino acid residues: 157V, 163K, 195R, and 212A.

In a particular embodiment, the constant region is selected from the group of: Clambda27, Clambda67, Clambda6ΔS, Clambda7ΔS, Clambda27ΔS, and Clambda67ΔS as shown in FIG. 3.

In a third aspect, the invention relates to an antibody or antibody fragment comprising at least the constant region of the present invention.

In certain embodiments of the present invention, the constant region or the antibody or antibody fragment is isolated. In certain such embodiments, the isolated constant region or isolated antibody or antibody fragment is free from full-length constant region or antibody or antibody fragment (i.e. free from proteins with wild-type constant region) and/or free from other degradation products generated from wild-type protein.

In certain embodiments, the antibody fragment is a functional antibody fragment.

In a fourth aspect, the present invention relates to the use of a constant region of an antibody lambda light chain according to the present invention in the construction of an antibody or antibody fragment, comprising the step of attaching said constant region to an antibody variable domain.

In a fifth aspect, the present invention relates to nucleic acid sequence encoding the constant region of an antibody lambda light chain according to the present invention, or the antibody or antibody fragment of the present invention.

In a sixth aspect, the present invention relates to a vector comprising the nucleic acid sequence according to the present invention.

In a seventh aspect, the present invention relates to a host cell comprising the nucleic acid sequence according to the present invention, or the vector according to the present invention.

In an eight aspect, the present invention relates to a method for generating the constant region of the present invention, or the antibody or functional fragment thereof of to the present invention, comprising the step of expressing the nucleic acid sequence according to the present invention, or the vector according to the present invention, either in vitro of from an appropriate host cell, including the host cell according to the present invention.

In a ninth aspect, the present invention relates to pharmaceutical compositions comprising an antibody molecule or functional fragment thereof comprising the constant region of an antibody lambda light chain according to the present invention, and optionally a pharmaceutically acceptable carrier and/or excipient.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). The term "pharmaceutically acceptable" may also mean approved by a regulatory agency of the Federal or a state government or listed in the U.S. Pharmacopeia or other generally recognized pharmacopeia for use in mammals, and more particularly in humans.

In the context of the present invention, the term "about" or "approximately" means between 90% and 110% of a given value or range.

The term "carrier" applied to pharmaceutical compositions of the invention refers to a diluent, excipient, or vehicle with which an active compound (e.g., a bispecific antibody fragment) is administered. Such pharmaceutical carriers may be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by A. R. Gennaro, 20th Edition.

The active ingredient (e.g., a modified antibody fragment) or the composition of the present invention may be used for the treatment of at least one disease or disorders, wherein the treatment is adapted to or appropriately prepared for a specific administration as disclosed herein (e.g., to once-a-day, twice-a-day, or three times a day administration). For this purpose the package leaflet and/or the patient information contains corresponding information.

The active ingredient (e.g., the modified antibody molecule or fragment thereof) or the composition of the present invention may be used for the manufacture of a medicament for the treatment of at least one disease or disorder, wherein the medicament is adapted to or appropriately prepared for a specific administration as disclosed herein (e.g., to once-a-day, twice-a-day, or three times a day administration). For this purpose the package leaflet and/or the patient information contains corresponding information.

EXAMPLES

The following examples illustrate the invention without limiting its scope.

Example 1: Antibody Optimization

In humans, several different isotypes of the constant domain of lambda light chains (hereinafter CL) occur naturally, with different amino acid sequences encoded by different IGLC genes. As reviewed by Jefferis (2009), the number of IGLC genes in humans varies between 7 and 11 depending on individual haplotypes. These isotypes can also be distinguished serologically. In the 7-gene haplotype IGLC1, IGLC2, IGLC3 and IGLC7 are functional, IGLC4 and IGLC5 are pseudogenes and IGLC6 is either functional in a rare haplotype or a pseudogene encoding a truncated sequence.

In libraries of recombinant human Fab fragments, the constant domain CL2 (encoded by IGLC2) is frequently used as the chosen isotype. However, a general problem for lambda antibody drug development is that the level of constant region degradation can be very high when antibodies comprising a CL2 domain are expressed in $E.$ $coli$. Surprisingly, in the present invention we found that using engineered CL domains with only few amino acid changes compared to the naturally occurring CL domains can significantly reduce the level of constant region degradation during $E.$ $coli$ expression of Fab fragments, resulting in a significantly higher amount of intact Fab fragment being produced. It is anticipated that the invention will be useful for the generation of more efficient phage display libraries of lambda antibodies and for the performance of more effective screening campaigns of lambda antibody clones.

Some of the degradation products that occur during $E.$ $coli$ expression of lambda Fab fragments can be visualised by SDS-PAGE, as illustrated in FIG. 1. FIG. 1 shows the situation seen when a lambda Fab fragment is purified via the superantigen protein A that binds to the VH domain of some human VH3 antibodies. A human VH3-containing lambda Fab fragment was expressed in TG1 $E.$ $coli$ cells for 16 h at 30° C., using modified Terrific Broth (Carl Roth) as medium. All Fab protein containing an intact VH domain was then purified from the culture supernatant on protein A resin (Millipore). Purified protein was separated on a non-reducing SDS-PAGE 4-12% gradient gel (LifeTech) and visualised using SafeStain (LifeTechnologies). The following major products purified are seen on the non-reducing gel: (A) full Fab fragment with heavy and light chains covalently associated via a disulphide bond between a cysteine in an IgG1 hinge fragment that was appended to the CH1 domain and Cysteine 214 (Kabat numbering; see FIG. 3; numbering based on numbering system used in Kabat, E. A. et al., Sequences of proteins of immunological interest. 5th Edition—US Department of Health and Human Services, NIH publication n° 91-3242, p 647 (1991).) near the C-terminus of the CL domain. (B) Heavy and light chains of apparently full-length, which can also be purified via protein A in an associated state as full Fab fragment but lack oxidation of the potential disulphide bond between a cysteine in the IgG1 hinge fragment that was appended to the CH1 domain and Cysteine 214 (IMGT numbering) near the C-terminus of the CL domain. (C) A fragment of the heavy chain that was shown to start with the intact, mature N-terminal VH sequence (this was demonstrated by N-terminal peptide sequencing—data not shown) but is truncated as seen by its migration at a smaller size. (D) A fragment of the light chain that was shown to start with the intact, mature N-terminal VL sequence (this was demonstrated by N-terminal peptide sequencing—data not shown) but is truncated as seen by its migration at a smaller size. This fragment can be purified if it is associated with fragment (C) or with full-length heavy chain, which is the upper band within fragment (B), if any is available and not associated with full-length light chain. It is unknown whether the truncated fragments C and D are the result of CL degradation by proteolytic cleavage, premature termination of translation or another mechanism, but these two degradation products are consistently observed following protein A purification of lambda Fab fragments and can be presumed to be generally present during E. coli expression of lambda Fab fragments. Importantly, if Fab fragments are purified via a C-terminal tag on the CH1 domain, which is a more frequently used strategy, the degradation products pointed out in FIG. 1 are produced but not purified and therefore not seen in SDS-PAGE. This is equivalent to the situation in Fab phage library production, where the degradation products can be produced but only full-length Fab fragments can be correctly incorporated into phage particles due to a linker or engineered free Cysteine present at one of the C-termini. It is also equivalent to the situation in Fab screening in microtiter plates, where the degradation products can be produced but only full-length Fab fragments are detected due to an epitope tag fused to one of the C-termini or due to an epitope located within one of the constant domains (see above).

We decided to quantify the correctly folded full Fab (with or without the C-terminal disulphide bond), i.e. the correctly folded portion of Bands (A) and (B) in FIG. 1, relative to any measurably folded degradation product, presumed to be mostly the associated portion of degradation products (C) and (D). If degradation products (C) and (D) are associated in such a way that they form a functional binding site, their presence but inability to detect them due to lack of epitope tags could seriously impair the efficiency of screening assays. For the desired relative quantification of intact Fab and folded degradation product we used differential scanning calorimetry (DSC) as described below. In the DSC analysis of lambda Fab fragments produced in E. coli and purified on protein A resin, two very distinct unfolding events could regularly be observed: at a lower temperature the unfolding event corresponding to the unfolding of folded degradation product and, at a higher temperature, the unfolding event corresponding to the unfolding of correctly folded full Fab fragment. When the correctly folded full Fab fragment had a good stability with a melting temperature (TM) greater than 85° C. in pure 1×PBS pH7.4, the folded degradation product also became more stable and became more abundant, as seen by an increased calorimetric enthalpy of denaturation $\Delta H$, i.e. the area under the peak in DSC.

Importantly, when lambda antibodies comprising a human wild-type CL2 constant domain had a very high stability of the full Fab fragment with a TM of approximately 90° C. in pure 1×PBS pH7.4, the folded degradation product was so abundant that the calorimetric enthalpy of denaturation $\Delta H1$, corresponding to the denaturation of the degradation product, reached more than 50% of the total calorimetric enthalpy of denaturation ($\Delta H1+\Delta H2$, in which $\Delta H2$ corresponds to the denaturation of the full correctly folded Fab fragment).

We then tested additional wild-type human lambda constant domains, CL6 (encoded by the human IGLC6 gene) and CL7 (encoded by the human IGLC7 gene), as well as novel, engineered human lambda constant domains. All of the constant domains were tested with the same variable region and were expressed and purified from the same vector under the same conditions. Two independent duplicate batches of each Fab were produced and analysed. The results of the DSC analysis are summarised in Table 1 and illustrated in FIG. 2.

It was found that Fab fragments comprising a wild-type human CL7 domain were produced with slightly more intact full Fab fragment as compared to those comprising a wild-type human CL2 domain, while Fab fragments comprising a wild-type human CL6 domain were produced with significantly more intact full Fab fragment as compared to those comprising a wild-type human CL2 domain.

Surprisingly, it was possible to engineer novel human CL domains that resulted in the production of significantly more intact full Fab fragment as compared to those comprising a corresponding wild-type human CL domain. First, when the Fab fragment was produced with an engineered CL domain in which residues 112 to 151 are identical to human CL2 and residues 137 to 215 are identical to human CL7 (with residues 137 to 151 being identical to both; hereinafter referred to as CL27), expressed antibodies contained much more intact full Fab fragment as compared to those comprising either wild-type human CL2 domain or wild-type human CL7 domain. Second, when the Fab fragment was produced with an engineered CL domain in which residues 112 to 194 are identical to human CL6 and residues 164 to 151 are identical to human CL7, with residues 164 to 194 being identical to both; hereinafter referred to as CL67), expressed antibodies also contained more intact full Fab fragment than those comprising wild-type human CL7 domain. Finally, it was extremely surprising to discover that when Fab fragments were produced with an engineered CL domain in which the C-terminal Serine residue 215 had been deleted (hereinafter referred to as CL6$\Delta$S, CL7$\Delta$S, CL27$\Delta$S and CL67$\Delta$S) expressed antibodies contained much more intact full Fab fragment as compared to those bearing the wild-type C-terminal Serine residue. This was especially surprising as the existence of an amino acid in this position appears to be completely conserved, even across other species where the residue may be an amino acid other than Serine (reference: IMGT protein displays).

Antibody Expression and Purification

TG1 E. coli clones bearing Fab expression constructs were grown in LB, 2×YT and modified TB media, purchased from Carl Roth, which were supplemented with Carbenicillin and glucose, purchased from VWR. Antibody expression in liquid cultures was performed overnight in Erlenmeyer flasks in a shaking incubator and was induced by the addition of isopropyl-β-D-thiogalactopyranoside (IPTG), purchased from Carl Roth, to the growth medium. Culture supernatants containing secreted Fab fragments were clarified by centrifugation of the expression cultures. Clarified culture supernatants were passed through columns fitted with gravity flow funnels and packed with a 0.5% culture volume of ProSep vA Ultra resin (Millipore), to achieve binding of Fab fragments. Resins were then washed once using 25 bed volumes of 2×PBS pH 7.4, purchased from Invitrogen, washed once using 4 bed volumes of a buffer containing 10 mM Tris pH 6.8 and 100 mM NaCl, purchased from VWR, and eluted using a buffer containing 10 mM citric acid pH3 and 70 mM NaCl, purchased from VWR. Eluted Fab fragments were neutralized by adding an 8% volume of 1M Tris pH 8.0. Neutralized purified Fab fragments were buffer exchanged into pure 1×PBS pH 7.4 (containing 1.06 mM $KH_2PO_4$, 2.97 mM $Na_2HPO_4×7H2O$, 155.17 mM NaCl and no other supplements; Invitrogen catalogue No. 10010056), using illustra NAP-5 desalting columns from GE Healthcare, according to manufacturer's instructions, and quantified by absorbance reading at 280 nm.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

To the extent possible under the respective patent law, all patents, applications, publications, test methods, literature, and other materials cited herein are hereby incorporated by reference.

TABLE 1

Results of Calorimetric Analysis

| CL domain | Clone | Batch | Concentration [mM] | TM1 (degradation product) | ΔH1 | Error on ΔH1 | TM2 (full intact Fab) | ΔH2 | Error on ΔH2 | ΔH1 + ΔH2 | % intact |
|---|---|---|---|---|---|---|---|---|---|---|---|
| CL7 | L17.1 | 1 | 0.013544 | 78.34 | 197900 | 1560 | 89.71 | 202700 | 1490 | 400600 | 50.5991 |
| CL7 | L17.1 | 2 | 0.011273 | 78.29 | 174600 | 1530 | 89.65 | 187400 | 1440 | 362000 | 51.76796 |
| CL27 | L17.2 | 1 | 0.013826 | 78.3 | 179900 | 1290 | 89.65 | 211900 | 1230 | 391800 | 54.08372 |
| CL27 | L17.2 | 2 | 0.011649 | 78.28 | 164200 | 1630 | 89.85 | 202200 | 1500 | 366400 | 55.18559 |
| CL6 | L17.3 | 1 | 0.01388 | 78.23 | 162100 | 1450 | 89.8 | 221700 | 1330 | 383800 | 57.76446 |
| CL6 | L17.3 | 2 | 0.011931 | 77.97 | 147800 | 1620 | 89.8 | 214600 | 1490 | 362400 | 59.21634 |
| CL67 | L17.4 | 1 | 0.014296 | 78.31 | 183400 | 1720 | 89.68 | 199700 | 1590 | 383100 | 52.12738 |
| CL67 | L17.4 | 2 | 0.011139 | 78.28 | 174200 | 1950 | 89.7 | 201100 | 1800 | 375300 | 53.5838 |
| CL2 | L17.5 | 1 | 0.012173 | 78.49 | 217000 | 1610 | 89.86 | 207700 | 1520 | 424700 | 48.90511 |
| CL2 | L17.5 | 2 | 0.010171 | 78.31 | 199100 | 1680 | 89.87 | 196500 | 1580 | 395600 | 49.67139 |
| CL7ΔS | L18.1 | 1 | 0.01255 | 78.3 | 168400 | 1630 | 89.79 | 229200 | 1510 | 397600 | 57.64588 |
| CL7ΔS | L18.1 | 2 | 0.01134 | 78.28 | 172900 | 1650 | 89.78 | 235700 | 1510 | 408600 | 57.68478 |
| CL27ΔS | L18.2 | 1 | 0.0122 | 77.98 | 135800 | 1950 | 90.01 | 238700 | 1760 | 374500 | 63.73832 |
| CL27ΔS | L18.2 | 2 | 0.012375 | 78.15 | 151800 | 1660 | 89.9 | 243400 | 1510 | 395200 | 61.58907 |
| CL6ΔS | L18.3 | 1 | 0.013208 | 77.88 | 137900 | 1780 | 89.92 | 259600 | 1580 | 397500 | 65.30818 |
| CL6ΔS | L18.3 | 2 | 0.013248 | 77.93 | 130500 | 1880 | 89.96 | 257900 | 1690 | 388400 | 66.40062 |
| CL67ΔS | L18.4 | 1 | 0.013221 | 78.27 | 157200 | 1920 | 89.77 | 241100 | 1750 | 398300 | 60.53226 |
| CL67ΔS | L18.4 | 2 | 0.013235 | 78.31 | 161600 | 1860 | 89.74 | 241600 | 1700 | 403200 | 59.92063 |

Determination of Calorimetric Enthalpy of Denaturation

The thermal denaturation of protein A-purified, buffer-exchanged Fab fragments was analysed in 1×PBS pH 7.4 (Invitrogen catalogue No. 10010056) using differential scanning calorimetry (DSC). For all measurements, a capillary cell microcalorimeter equipped with autosampler and controlled by VPViewer2000 CapDSC software from MicroCal was used. All Fab fragments were scanned against pure buffer containing no antibody (1×PBS pH 7.4; Invitrogen catalogue No. 10010056). The scan parameters were set to analyse a temperature window from 32° C. to between 107° C. and 115° C., with a pre-scan thermostat of 2 min, a post-scan thermostat of 0 min and no gain. The scan rate was set to 240° C. per hour. The data analysis was performed using Origin 7.0 software from MicroCal and was automated to avoid any subjective user input. First, pure PBS scanned against pure PBS was used for reference subtraction. Second, the scan was normalised for protein concentration using the absorbance determined at 280 nm and the calculated extinction coefficient for each Fab fragment. Third, the displayed data range was set to be 60° C. to 107° C. Fourth, the baseline was subtracted using the "linear connect" function. Fourth, the two peaks corresponding to folded degradation product and intact full Fab were identified using the "pick peaks" function, using search angle parameters of 5 for width and 5 for height as well as 5 for minimum height. Fifth, data were fitted to the Non-2-State model with variable H1 and variable Hv1, using 200 Levenberg-Marquardt iterations. Finally, the proportion of correctly folded full Fab was calculated on the basis that it approximately equals ΔH2/(ΔH1+ΔH2).

REFERENCES

Aburatani T, Ueda H, Nagamune T.
Importance of a CDR H3 basal residue in V(H)/V(L) interaction of human antibodies.
J Biochem. 2002 November; 132(5):775-82.
Al-Lazikani B, Lesk A M, Chothia C.
J Mol Biol. 1997 Nov. 7; 273(4):927-48.
Standard conformations for the canonical structures of immunoglobulins.
Arndt K M, Müller K M, Plückthun A.
Helix-stabilized Fv (hsFv) antibody fragments: substituting the constant domains of a Fab fragment for a heterodimeric coiled-coil domain.
J Mol Biol. 2001 Sep. 7; 312(1):221-8.
Barthelemy P A, Raab H, Appleton B A, Bond C J, Wu P, Wiesmann C, Sidhu S S.
Comprehensive analysis of the factors contributing to the stability and solubility of autonomous human VH domains.
J Biol Chem. 2008 Feb. 8; 283(6):3639-54. Epub 2007 Nov. 28.
Carter P, Presta L, Gorman C M, Ridgway J B, Henner D, Wong W L, Rowland A M, Kotts C, Carver M E, Shepard H M.
Humanization of an anti-p185HER2 antibody for human cancer therapy.
Proc Natl Acad Sci USA. 1992 May 15; 89(10):4285-9.
Chothia C, Lesk A M, Gherardi E, Tomlinson I M, Walter G, Marks J D, Llewelyn M B, Winter G.
Structural repertoire of the human VH segments.
J Mol Biol. 1992 Oct. 5; 227(3):799-817.
Davies J, Riechmann L.

'Camelising' human antibody fragments: NMR studies on VH domains.
FEBS Lett. 1994 Feb. 21; 339(3):285-90.
Davies J, Riechmann L.
Single antibody domains as small recognition units: design and in vitro antigen selection of camelized, human VH domains with improved protein stability.
Protein Eng. 1996 June; 9(6):531-7.
de Wildt R M, Hoet R M, van Venrooij W J, Tomlinson I M, Winter G.
Analysis of heavy and light chain pairings indicates that receptor editing shapes the human antibody repertoire.
J Mol Biol. 1999 Jan. 22; 285(3):895-901.
Demarest S J, Chen G, Kimmel B E, Gustafson D, Wu J, Salbato J, Poland J, Elia M, Tan X, Wong K, Short J, Hansen G.
Engineering stability into *Escherichia coli* secreted Fabs leads to increased functional expression.
Protein Eng Des Sel. 2006 July; 19(7):325-36. Epub 2006 May 3.
Dottorini T, Vaughan C K, Walsh M A, LoSurdo P, Sollazzo M.
Crystal structure of a human VH: requirements for maintaining a monomeric fragment.
Biochemistry. 2004 Jan. 27; 43(3):622-8.
Dudgeon K, Famm K, Christ D.
Sequence determinants of protein aggregation in human VH domains.
Protein Eng Des Sel. 2009 March; 22(3):217-20. Epub 2008 Oct. 28,
(A) Ewert S, Huber T, Honegger A, Plückthun A.
Biophysical properties of human antibody variable domains.
J Mol Biol. 2003 Jan. 17; 325(3):531-53.
(B) Ewert S, Honegger A, Plückthun A.
Structure-based improvement of the biophysical properties of immunoglobulin VH domains with a generalizable approach.
Biochemistry. 2003 Feb. 18, 42(6):1517-28.
Fellouse F A, Li B, Compaan D M, Peden A A, Hymowitz S G, Sidhu S S.
Molecular recognition by a binary code.
J Mol Biol. 2005 May 20; 348(5):1153-62. Epub 2005 Apr. 1.
Fellouse F A, Barthelemy P A, Kelley R F, Sidhu S S.
Tyrosine plays a dominant functional role in the paratope of a synthetic antibody derived from a four amino acid code.
J Mol Biol. 2006 Mar. 17; 357(1):100-14. Epub 2005 Dec. 19.
Fellouse F A, Esaki K, Birtalan S, Raptis D, Cancasci V J, Koide A, Jhurani P, Vasser M, Wiesmann C, Kossiakoff A A, Koide S, Sidhu S S.
High-throughput generation of synthetic antibodies from highly functional minimalist phage-displayed libraries.
J Mol Biol. 2007 Nov. 2; 373(4):924-40. Epub 2007 Aug. 19.
Garber E, Demarest S J.
A broad range of Fab stabilities within a host of therapeutic IgGs.
Biochem Biophys Res Commun. 2007 Apr. 13; 355(3):751-7. Epub 2007 Feb. 16.
Hoet R M, Cohen E H, Kent R B, Rookey K, Schoonbroodt S, Hogan S, Rem L, Frans N, Daukandt M, Pieters H, van Hegelsom R, Neer N C, Nastri H G, Rondon I J, Leeds J A, Hufton S E, Huang L, Kashin I, Devlin M, Kuang G, Steukers M, Viswanathan M, Nixon A E, Sexton D J, Hoogenboom H R, Ladner R C.
Generation of high-affinity human antibodies by combining donor-derived and synthetic complementarity-determining-region diversity.
Nat Biotechnol. 2005 March; 23(3):344-8. Epub 2005 Feb. 20.
Honegger A.
Engineering antibodies for stability and efficient folding.
Handb Exp Pharmacol. 2008; (181):47-68. Review.
Jefferis R. and Lefranc M.-P.,
Human immunoglobulin allotypes.
mAbs 1:4, 1-7; July/August 2009
(A) Jespers L, Schon O, Famm K, Winter G.
Aggregation-resistant domain antibodies selected on phage by heat denaturation.
Nat Biotechnol. 2004 September; 22(9):1161-5. Epub 2004 Aug. 8.
(B) Jespers L, Schon O, James L C, Veprintsev D, Winter G.
Crystal structure of HEL4, a soluble, refoldable human V(H) single domain with a germ-line scaffold.
J Mol Biol. 2004 Apr. 2; 337(4):893-903.
Jung S, Plückthun A.
Improving in vivo folding and stability of a single-chain Fv antibody fragment by loop grafting.
Protein Eng. 1997 August; 10(8):959-66.
Jung S, Honegger A, Plückthun A.
Selection for improved protein stability by phage display.
J Mol Biol. 1999 Nov. 19; 294(1):163-80.
Kabat E A, Wu U.
Identical V region amino acid sequences and segments of sequences in antibodies of different specificities. Relative contributions of VH and VL genes, minigenes, and complementarity-determining regions to binding of antibody-combining sites.
J Immunol. 1991 Sep. 1; 147(5):1709-19.
Kabat, E. A. et al., Sequences of proteins of immunological interest. 5th Edition—US Department of Health and Human Services, NIH publication n° 91-3242, p 647 (1991).
Knappik A, Ge L, Honegger A, Pack P, Fischer M, Wellnhofer G, Hoess A, Wölle J, Plückthun A, Virnekäs B.
Fully synthetic human combinatorial antibody libraries (HuCAL) based on modular consensus frameworks and CDRs randomized with trinucleotides.
J Mol Biol. 2000 Feb. 11; 296(1):57-86.
Lee C V, Liang W C, Dennis M S, Eigenbrot C, Sidhu S S, Fuh G.
High-affinity human antibodies from phage-displayed synthetic Fab libraries with a single framework scaffold.
J Mol Biol. 2004 Jul. 23; 340(5):1073-93.
Lefranc M P, Giudicelli V, Ginestoux C, Bodmer J, Müller W, Bontrop R, Lemaitre M, Malik A, Barbié V, Chaume D.
IMGT, the international ImMunoGeneTics database.
Nucleic Acids Res. 1999 Jan. 1; 27(1):209-12.
Martineau P, Betton J M.
In vitro folding and thermodynamic stability of an antibody fragment selected in vivo for high expression levels in *Escherichia coli* cytoplasm.
J Mol Biol. 1999 Oct. 1; 292(4):921-9.
Muller Y A, Heiring C, Misselwitz R, Welfle K, Welfle H.
The cystine knot promotes folding and not thermodynamic stability in vascular endothelial growth factor.
J Biol Chem. 2002 Nov. 8; 277(45):43410-6.
Nieba L, Honegger A, Krebber C, Plückthun A.
Disrupting the hydrophobic patches at the antibody variable/constant domain interface: improved in vivo folding and physical characterization of an engineered scFv fragment.

Protein Eng. 1997 April; 10(4):435-44.
Ohage E C, Graml W, Walter M M, Steinbacher S, Steipe B.
Beta-turn propensities as paradigms for the analysis of structural motifs to engineer protein stability.
Protein Sci. 1997 January; 6(1):233-41.
Ohage E, Steipe B.
Intrabody construction and expression. I. The critical role of VL domain stability.
J Mol Biol. 1999 Sep. 3; 291(5):1119-28.
Persson M A.
Twenty years of combinatorial antibody libraries, but how well do they mimic the immunoglobulin repertoire?
Proc Natl Acad Sci USA. 2009 Dec. 1; 106(48):20137-8. Epub 2009 Nov. 23. No abstract available.
Proba K, Wörn A, Honegger A, Pluckthun A.
Antibody scFv fragments without disulfide bonds made by molecular evolution.
J Mol Biol. 1998 Jan. 16; 275(2):245-53.
Retter I, Althaus H H, Münch R, Müller W.
VBASE2, an integrative V gene database.
Nucleic Acids Res. 2005 Jan. 1; 33(Database issue):D671-4.
Ribnicky B, Van Blarcom T, Georgiou G.
A scFv antibody mutant isolated in a genetic screen for improved export via the twin arginine transporter pathway exhibits faster folding.
J Mol Biol. 2007 Jun. 8; 369(3):631-9. Epub 2007 Mar. 31.
Riechmann L.
Rearrangement of the former VL interface in the solution structure of a camelised, single antibody VH domain.
J Mol Biol. 1996 Jun. 28; 259(5):957-69.
Rothe C, Urlinger S, Löhning C, Prassler J, Stark Y, Jäger U, Hubner B, Bardroff M, Pradel I, Boss M, Bittlingmaier R, Bataa T, Frisch C, Brocks B, Honegger A, Urban M.
The human combinatorial antibody library HuCAL GOLD combines diversification of all six CDRs according to the natural immune system with a novel display method for efficient selection of high-affinity antibodies.
J Mol Biol. 2008 Feb. 29; 376(4):1182-200. Epub 2007 Dec. 15.
Silacci M, Brack S, Schirru G, Mårlind J, Ettorre A, Merlo A, Viti F, Neri D.
Design, construction, and characterization of a large synthetic human antibody phage display library.
Proteomics. 2005 June; 5(9):2340-50.
Steipe B, Schiller B, Plückthun A, Steinbacher S.
Sequence statistics reliably predict stabilizing mutations in a protein domain.
J Mol Biol. 1994 Jul. 15; 240(3):188-92.
Sterner R, Liebl W.
Thermophilic adaptation of proteins.
Crit Rev Biochem Mol Biol. 2001; 36(1):39-106.
Tan P H, Sandmaier B M, Stayton P S.
Contributions of a highly conserved VH/VL hydrogen bonding interaction to scFv folding stability and refolding efficiency.
Biophys J. 1998 September; 75(3):1473-82.
Tanha J, Xu P, Chen Z, Ni F, Kaplan H, Narang S A, MacKenzie C R.
Optimal design features of camelized human single-domain antibody libraries.
J Biol Chem. 2001 Jul. 6; 276(27):24774-80. Epub 2001 May 2.
Tomlinson I M, Cox J P, Gherardi E, Lesk A M, Chothia C.
The structural repertoire of the human V kappa domain.
EMBO J. 1995 Sep. 15; 14(18):4628-38.
Wetzel S K, Settanni G, Kenig M, Binz H K, Plückthun A.
Folding and unfolding mechanism of highly stable full-consensus ankyrin repeat proteins.
J Mol Biol. 2008 Feb. 8; 376(1):241-57.
Wörn A, Plückthun A.
Stability engineering of antibody single-chain Fv fragments.
J Mol Biol. 2001 Feb. 2; 305(5):989-1010. Review.

I claim:

1. A constant region of an antibody lambda light chain, comprising a single constant region of a Clambda7 antibody lambda light chain according to SEQ ID NO:3, wherein the C-terminal serine at position 215 is deleted and wherein said constant region has an isoleucine residue at position 136 and optionally one or more of the following amino acid residues: 145K, 156N, 157T, and 163T.

2. The constant region of claim 1, wherein the constant region is selected from the group of: Clambda27ΔS according to SEQ ID NO:8, and Clambda67ΔS according to SEQ ID NO:9.

3. An antibody or antibody fragment comprising at least the constant region of claim 1.

4. A method for construction of an antibody or antibody fragment, comprising the step of attaching a constant region of an antibody lambda light chain according to claim 1 to an antibody variable domain.

5. A nucleic acid sequence encoding the constant region of an antibody lambda light chain according to claim 1.

6. An isolated vector comprising the nucleic acid sequence of claim 5.

7. An isolated host cell comprising the nucleic acid sequence of claim 5.

8. A method for generating the constant region of claim 1, comprising the step of expressing the nucleic acid sequence encoding the constant region of an antibody lambda light chain of claim 1.

9. A pharmaceutical composition comprising the antibody or antibody fragment of claim 3, and optionally a pharmaceutically acceptable carrier and/or excipient.

10. An antibody or antibody fragment comprising at least the constant region of claim 2.

11. A method for construction of an antibody or antibody fragment, comprising the step of attaching a constant region of an antibody lambda light chain according to claim 2 to an antibody variable domain.

12. A nucleic acid sequence encoding the constant region of an antibody lambda light chain according to claim 2.

13. A nucleic acid sequence encoding the constant region of an antibody lambda light chain according to the antibody or antibody fragment of claim 3.

14. An isolated host cell comprising the vector of claim 6.

15. A method for generating the constant region of claim 2, comprising the step of expressing the nucleic acid sequence encoding the constant region of an antibody lambda light chain of claim 2.

\* \* \* \* \*